Oct. 28, 1930. H. J. BOSWORTH Re. 17,845

LIGHT SUPPORT

Original Filed July 21, 1924 2 Sheets-Sheet 1

Witness

Harry R. White

Inventor:

Harry J. Bosworth

By Avery Jackson, Bettcher & Dimmer

Attys.

Oct. 28, 1930. H. J. BOSWORTH Re. 17,845

LIGHT SUPPORT

Original Filed July 21, 1924 2 Sheets-Sheet 2

Witness:

Harry C. L. White.

Inventor

Harry J. Bosworth

By Brown Jackson Boettcher & Dienner

Attys

Reissued Oct. 28, 1930 Re. 17,845

UNITED STATES PATENT OFFICE

HARRY J. BOSWORTH, OF CHICAGO, ILLINOIS, ASSIGNOR TO HARRY J. BOSWORTH COMPANY, OF CHICAGO, ILLINOIS, A CORPORATION OF ILLINOIS

LIGHT SUPPORT

Original No. 1,644,231, dated October 4, 1927, Serial No. 727,166, filed July 21, 1924. Application for reissue filed November 18, 1927. Serial No. 234,285.

The present invention relates to light supports and more particularly to an improved electric lamp bracket especially adapted for use with the equipment employed by dentists, physicians and the like, although it may be employed wherever found suitable.

An object of the invention is the provision of a light support capable of angular adjustment in different directions, as for example, in a vertical and in a horizontal plane and extensible to permit adjustment of the arc or radius of angular adjustment, also counterbalanced to be retained in any position into which the light is moved or adjusted, with means for varying or adjusting the counterbalancing action to counterbalance the light in its various extended and retracted positions, as well as in its various angular positions.

Another object is the provision of a generally improved and simplified construction that may be inexpensively produced, one that is strong and durable and adapted for quick and easy and more or less universal intallation.

The invention provides a construction in which the foregoing is attained and, at the same time, carrying of an electric conductor or conductors in the support or training or threading of same through the support is permitted without danger of injuring the conductor or conductors in the adjustment of the support or bracket to its various positions or by the counterbalancing action set up or counterbalance adjusting means provided and in which none of said actions is impaired by the carrying of the conductor or conductors in the support.

To acquaint those skilled in the art with the manner of and means for practicing my present invention, I will now describe in connection with the accompanying drawings forming a part of this specification, a particular embodiment of the invention.

In the drawings:—

Figure 1:
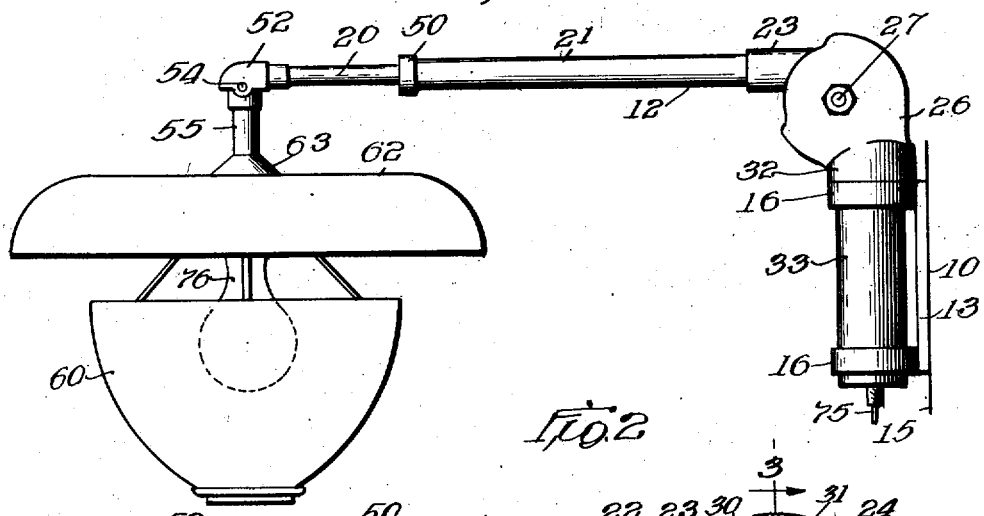
Fig. 1 is a side elevational view of a light support embodying the improvements of my invention.
Figure 2:
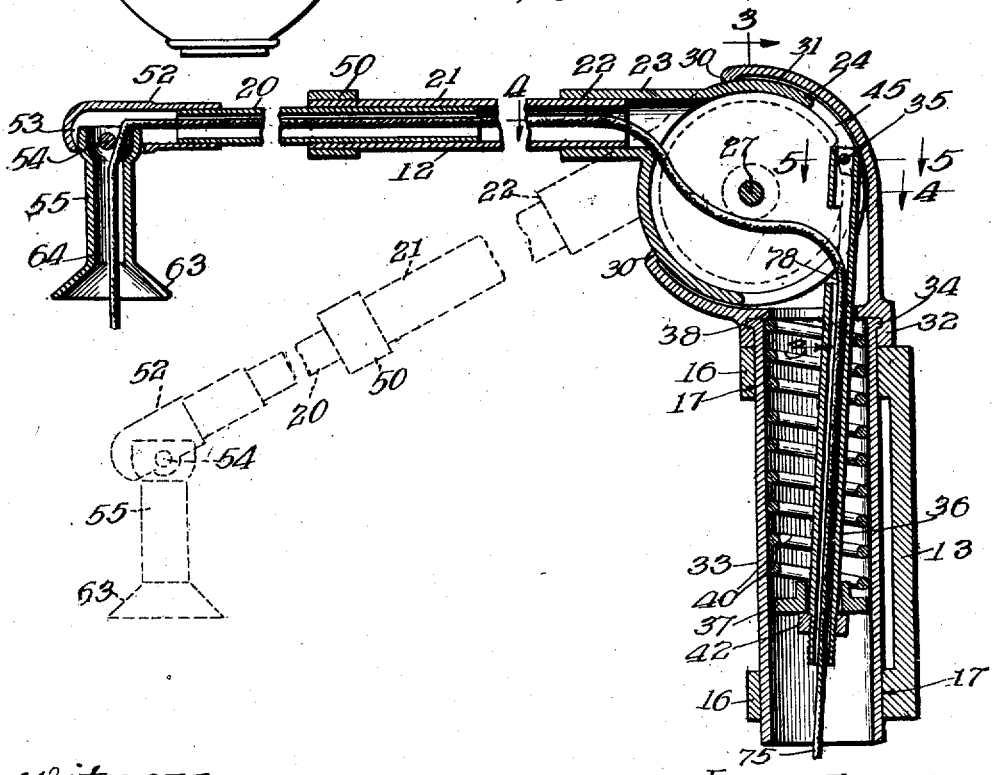
Fig. 2 is a vertical sectional view longitudinally through the carrying arm of the support and through the mounting and light or lamp carrying ends thereof.
Figure 3:
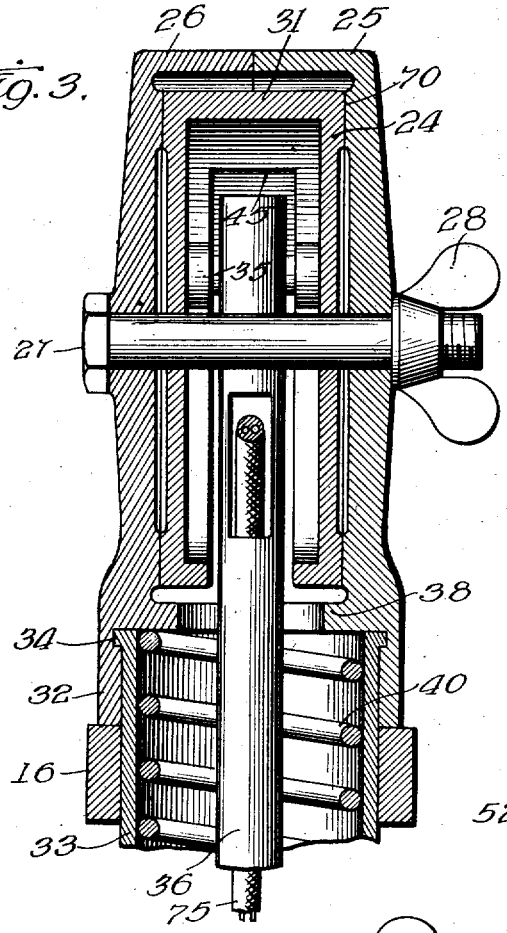
Fig. 3 is an enlarged vertical section on line 3—3 of Fig. 2.
Figure 5:
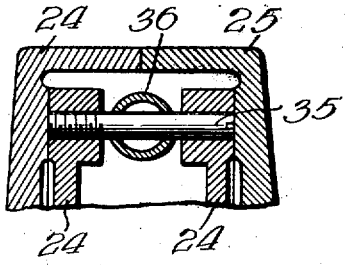
Fig. 5 is a detail section on line 5—5 of Fig. 2.
Figure 6:
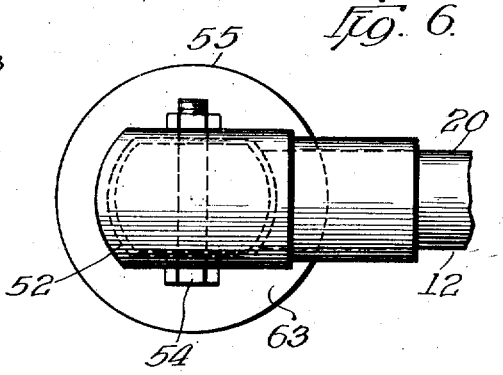
Fig. 6 is a plan view of the lamp or light carrying end of the arm.
Figure 4:
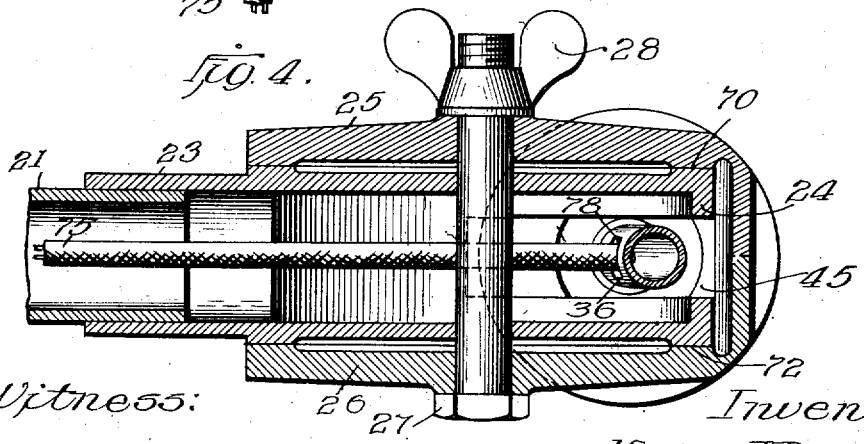
Fig. 4 is a horizontal section on line 4—4 of Fig. 2.

Referring to the drawings, 10 designates the supporting bracket of the fixture, and 12 the light or lamp support in its entirety.

The supporting bracket 10 comprises a base 13 which may be apertured or otherwise suitably formed for bolting or other suitable attachment to the wall or other support 15. The base 13 has outwardly extending ends 16 provided with concentric openings 17.

The light or lamp carrying arm comprises a pair of telescoping tubes 20 and 21, the tube 21 being suitably secured at 22 in the tubular projection 23 of a mounting head 24. The head 24 is mounted for swinging movement in a vertical plane between a pair of cooperating head members 25 and 26 upon a pin or post comprising a bolt 27 which extends through the head members 25 and 26 and through the side walls of the head member 24 and has threaded engagement with a wing nut 28. The head members 25 and 26 have inturned margins or flanges 30 which engage the circular wall 31 of the head member 24 and provide a smooth, balanced swinging movement in a vertical direction of the light arm about the axis of the pin or bolt 27.

The head members 25 and 26 have depending semi-circular portions 32 for receiving the upper end of a tubular post or rotatable cylinder 33, said post 33 having at its upper end a circumferential flange or bead 34 for securing the parts against separation when the head members are clamped together. Post 33 is rotatably mounted in the concentric openings 17 of bracket 13, the lower edges of the depending semi-circular portions 32 of head members 25 and 26 affording a shoulder which engages the upper outturned end 16 of bracket 13 and thereby supports the mounting post 33 therein.

Pivoted at its upper end between the sides of head member 24 upon a pin 35 secured at its opposite ends in the side walls of head member 24, is an arm 36. This arm 36 which is preferably tubular, for a purpose which will hereinafter appear, extends down into the tubular post 33 and slidable upon said arm within the post 33 is a collar 37. The arm 36 forms a plunger arm guided in the cylinder 33 and fully movable without interfering with or injuring the conductors. Interposed between collar 37 and an inwardly extending flange 38 on head members 25 and 26 is a coiled spring 40. A nut 42 threaded upon the arm 36 transmits the tension of spring 40 to the arm 36 and thereby to the light supporting arm of the fixture, and said nut 42 is adjustable on the arm 36 for the purpose of adjusting the tension of spring 40. The circular wall 31 of head member 24 is cut away or removed at 45 to permit the upper end of arm 36 to extend between the side walls of said head member and to accommodate said arm in the various relative positions of it and the head member 24.

From the foregoing it will appear that the light supporting arm 12 is pivotally supported on the top of the cylinder 33. This disposes the support for this arm for convenient access below the pivotal mounting and permits maximum upward swing without the possibility of interference.

As already pointed out, the light carrying arm is extensible and retractible for the purpose of varying the distance of the light from the support and thereby the arc or path of movement in both planes of its swinging adjustment. This extension and retraction is secured by sliding movement of the tube 20 into and out of the tube 21. Although a nut or other suitable means may be provided for locking the tube 20 in any desired extended or retracted position, the tube 20 is preferably held by friction and the counterbalancing action so that a nut need not be loosened and tightened each time. Fixedly mounted upon the outer end of tube 20 is a light supporting fitting 52 having a downwardly opening mouth 53 in which and between the sides of the fitting is pivoted at 54 a pendant light support 55.

While the particular form of light may be widely varied, that shown comprises a lower translucent bowl or open topped globe 60 and an upper shade 62. The lower end of the pendant support 65 may be flared at 63 and internally threaded at 64 for mounting the shade and light thereon and the upper pivoted end is shown as being slightly enlarged. The pivotal mounting of the pendant support 65 permits the light to assume a vertical position in all angular and other adjusted positions of the support.

In use the arm 12 has pivotal or swinging movement in a vertical plane about pivot 27 and the light may be swung into any desired position about said pivot. The coiled spring 40 is adjusted to counterbalance the arm and light in its various positions about pivot 27 so that upon swinging the light into the desired position about pivot 27, it will be counterbalanced and thereby retained or held in said position by spring 40. The light may be swung in a horizontal plane by turning or rotation of post 33 in the openings 16 about the axis thereof, and the distance of the light from the support is increased or decreased, and its path of swinging movement about pivot 27 in a vertical plane and about post 33 in a horizontal plane may be thereby adjusted by extension or retraction of the telescoping arms 20 and 21. The simple extension or retraction of arm 20 thereby not only changes or adjusts the position of the light without further adjustment, but adjusts both arcs of swinging movement of the light. This, in combination with two angular or swinging of adjustments provided, permits substantially any desired positioning of the light about the support. The head members provide additional frictional resistance to turning and enclose and protect the flexible conductors.

To provide additional counterbalancing resistance or retention for the arm 12 as its length is increased, I provide the head members 25, 24 and 26 with cooperating frictionally engaging surfaces 70 and 72. As the length of the arm 12 is increased, a slight tightening up of wing nut 28 will increase the friction between surfaces 70 and 72 so that the spring 40 will again properly counterbalance the support or arm in its various angular positions. If the length of the arm 12 is further increased, the nut 28 may be again drawn up or tightened to further increase this resistance and thereby further increase the counterbalancing action. If the length of the arm 12 is decreased, loosening of the nut 28 will decrease the friction between the surfaces 70 and 72 with an accompanying decrease in the counterbalancing action, so that it will be apparent that the light may be properly counterbalanced in all its adjusted positions.

The conductors 75 which supply current to the lamp 76 are preferably of the flexible type. They lead into the lower open end of supporting tube 33, up into the lower open end of tubular arm 36, through arm 36 and out through an opening 78 in one side thereof below pivot 35 and adjacent pivot 27 and are trained through head 24 about pivot 27, out through the tubular arm 12 and down through pendant support 55 about pivot 54 to the lamp 76 with which they have suitable connection, as for example, by means of a standard "Edison" or any other preferred type of socket or connecting member. Owing to the manner in which the conductor extends through the tubular mounting post, tubular counterbalancing arm, open head and light carrying arm, there is no danger of twisting or other injury to the conductor by the swinging or other adjusting movement of the support. The counterbalancing means in no way interferes with the conductor nor does the conductor in any way interfere with the counterbalancing means nor with the various adjusting movements of the support. The parts are simple and relatively inexpensive in construction and assembly, and the support is strong and durable and adapted for quick and easy and more or less universal installation and the light is capable of angular adjustment in vertical and horizontal planes and it is also extensible and retractible from the support. The light and light arm are counterbalanced to be retained into any position into which adjusted and the cooperation of the head members 24, 25 and 26 with the nut 28 provides for conveniently adjusting the counterbalancing action to take care of extension and retraction of the light carrying arm. The bolt 27 forms the pivot about which the arm is adapted to be swung in a vertical plane and at the same time said bolt provides for increasing and decreasing the counter-balancing action to properly counterbalance the arm and light in its different extended and retracted positions. The support is easily adjusted and the light can be put just where it is needed without effort.

The upper shade 62 is preferably a diffusing shade and the lower shade is preferably of glass or other suitable translucent material, the opening between the shades being especially suitable for ventilating the lamp 76.

While I have described the invention in connection with the details of a particular embodiment, it is to be understood that various lights and fixtures may be carried at the outer end of the light arm and that other modifications and changes may be made within the scope of the invention.

The support is particularly adapted for wall mounting, but it is in nowise limited to such mounting, but may be mounted upon any other suitable support. In fact, it may be mounted on the drill supporting or other dental equipment about the patient's chair, for example, or it may be mounted interchangeably or in connection with a fan support, tool support, or other supports that are commonly employed with such equipment.

Use of my improved bracket for carrying a telephone or the like and for attaching an operating light to present dental units now on the market, is contemplated. The bracket provides for conveniently bringing the light up close to the field of operation, which has not been possible before.

I claim:—

1. In a support of the character described, the combination of a mounting bracket having relatively fixed support, a hollow post journaled to turn in said bracket upon a vertical axis, an extensible arm adapted for the reception at its outer end of an article to be supported and pivoted at its inner end upon a horizontal pivot carried by the upper end of said post for swinging movement about the horizontal axis of said pivot, friction means adjacent said pivot with externally exposed and quickly accessible means for adjusting said friction means for different extended and retracted conditions of said arm, spring means confined within said hollow post and operatively associated with the pivoted end of said arm for counter-balancing said arm in a given extended position and in accordance with the weight of the article supported thereby and means accessible from the lower end of said post for adjusting said counter-balancing spring independently of the adjustment of said friction means to provide a spring counter-balancing action in accordance with the weight of the article supported by said arm.

2. In a support of the character described, the combination of a mounting bracket having relatively fixed support, a hollow post journaled to turn in said bracket upon a vertical axis, an extensible arm adapted for the reception at its outer end of an article to be supported and pivoted at its inner end upon a horizontal pivot carried by the upper end of said post for swinging movement about the horizontal axis of said pivot, friction means adjacent said pivot with externally exposed and quickly accessible means for adjusting said friction means for different extended and retracted conditions of said arm, a rod pivoted to the inner end of the article supporting arm eccentrically of the horizontal pivot therefor and extending into the hollow post, spring means confined within said hollow post and operatively associated with said rod for counter-balancing said arm in a given extended position and in accordance with the weight of the article supported thereby and means on said rod and accessible from the lower end of said post for adjusting said counter-balancing spring independently of the adjustment of said friction means to provide a spring counter-balancing action in accordance with the weight of the article supported by said arm.

3. In a lighting fixture for the purpose specified, the combination of a wall bracket, a rotatable cylinder containing therein a plunger, a resisting spring contained within the cylinder, and a light-supporting arm pivotally supported on the top of the cylinder and provided with a portion pivoted to said plunger eccentrically of the pivotal support of said light-supporting arm on the top of the cylinder whereby the plunger tends to counter-balance the arm and retain it in a given position of adjustment.

In witness whereof, I hereunto subscribe my name this 15th day of November, 1927.

HARRY J. BOSWORTH.